United States Patent [19]

Swartz

[11] Patent Number: 4,681,839

[45] Date of Patent: Jul. 21, 1987

[54] SYSTEMS TO PRESERVE LIVING TISSUE

[76] Inventor: Mitchell R. Swartz, 16 Pembroke Rd., Weston, Mass. 02193

[21] Appl. No.: 422,038

[22] Filed: Sep. 23, 1982

[51] Int. Cl.$^4$ .......................... A01N 1/02; C12N 1/04; C12N 5/02; C12M 3/00

[52] U.S. Cl. ........................................ 435/1; 435/241; 435/260; 435/284; 435/287; 435/810

[58] Field of Search .................. 435/1, 240, 241, 284, 435/285, 286, 287, 260, 810

[56] References Cited

U.S. PATENT DOCUMENTS

| | | | |
|---|---|---|---|
| 3,022,783 | 2/1962 | Tucker, Jr. | 435/1 X |
| 3,717,199 | 2/1973 | Dienst | 435/1 X |
| 3,753,357 | 8/1973 | Schwartz | 435/1 X |
| 4,117,881 | 10/1978 | Williams et al. | 435/1 X |

*Primary Examiner*—Esther M. Kepplinger
*Assistant Examiner*—William J. Herald
*Attorney, Agent, or Firm*—Robert Shaw

[57] ABSTRACT

A system to maximize the probability of preserving living tissue separated from its host organism. The system includes a bag or other container to receive a liquid solution plus a biscuit that supplies both nutrients and other materials ordinarily supplied to the tissue by the host, as well as additional material helpful to the tissue during the sub-acute postraumatic period. The nutrients and other materials are introduced to the solution by a biscuit that is formed of the various necessary ingredients. The biscuit introduced to the solution containing the living tissue slowly dissolves therein. An outer housing receives the bag or other container with its contents. The outer housing, by use of ice or other heating/cooling measures, serves to maintain the tissue and its supporting mechanism at between about 2° C. and 20° C.

65 Claims, 3 Drawing Figures

SYSTEMS TO PRESERVE LIVING TISSUE

The present invention relates to methods and systems to maximize the probability of successfully preserving living tissue severed from its host living system.

The literature abounds with writings describing the re-implantation of severed appendages and the, albeit presently ephemeral, transplantation of cadaveric or homologous allografts, including allografts of skin, corneas, some internal organs (e.g., kidney, pancreas, lung and heart) plus nesidiogenesis of vital tissues. In all of these situations there exists the need to maximize the likelihood of a successful (i.e., functional) graft. The success is decisively related to many factors, including the time and incipient conditions, during which the appendage or tissue is severed from its host, before re-implantation. Frequently preservation may be particularly difficult following amputation as a consequence of traumatic catastrophic accident. In particular, failure to optimize the quality of the post-traumatic milieu creates an unnecessary rate-limiting obstruction to successful re-implantation. The present method and system provide both a superior milieu in the postpartum period, plus improved thermal and mechanical stability.

Accordingly, it is a principal object of the present invention to provide a novel method and system to preserve living tissue or tissues severed from its host.

Another object is to provide a method and system that is particularly useful to preserve human legs and arms that are catastrophically severed from the host.

Still another object is to enable improved preservation of germinal tissues, cloned cells and organs from selected animals, bacteria or cell lines.

These and still further objects are addressed hereinafter.

The foregoing objects are achieved, generally, in a method (and system) for preserving tissue that has been severed from its host, that comprises depositing the tissue in a bag containing a sterile liquid; introducing to the liquid within the bag a biscuit containing a pH buffer and electrolyte to maintain and preserve a quasistatic biochemical environment most favorable to thriving tissue or cells; and maintaining the liquid at a temperature favorable to survival of the tissue.

The invention is hereafter described with reference to the accompanying drawing in which.

Figure 1:
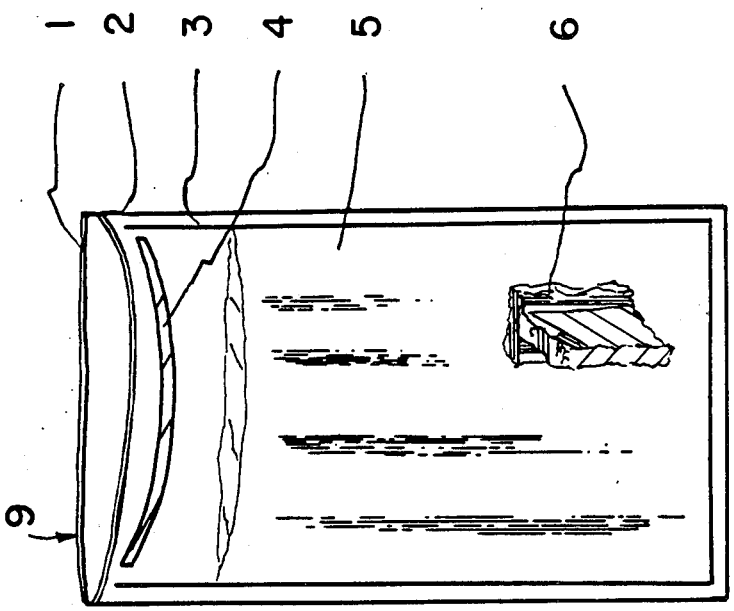
FIG. 1 is an isometric view of a bag and other elements of a system to preserve living tissue, cells and the like that have been severed from their host.
Figure 2:
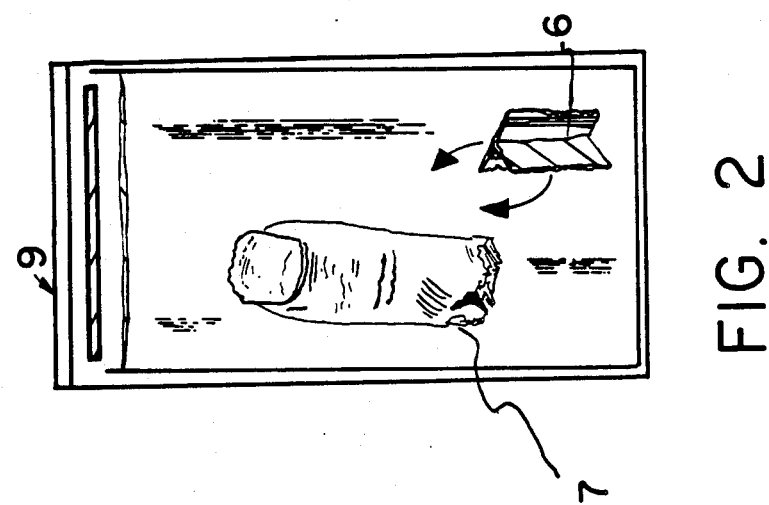
FIG. 2 shows the bag of FIG. 1 (slightly reduced in size) with a portion of a finger contained therein.
Figure 3:
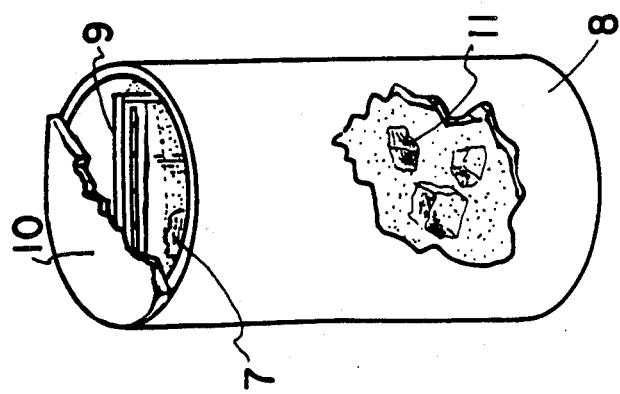
FIG. 3 shows isometrically and partially cutaway, an outer container with the bag (reduced in size), the finger and other system components within.

Turning now to the figures, the system labeled 101 in FIG. 3 serves to preserve living tissue (e.g., the severed finger shown at 7 in FIG. 2) that has been severed from its host. The system 101 includes a gas-permeable bag 9 to receive the tissue and a liquid solution 5 (e.g., water); the bag 9 provides a sterile environment for both the tissue and the solution during storage thereof. A T-shaped biscuit 6 is disposed within the bag, surrounded by the liquid 5. The biscuit 6 contains an electrolyte (e.g. potassium bicarbonate, potassium chloride, potassium dihydrogen phosphate, calcium salts) to maintain the cellular internal environment of the tissue and it contains, as well, a pH buffer (e.g., sodium and potassium bicarbonate). The T-shape form of biscuit results in a more uniform dissolution thereof within the solution, than would a spheroidal or pellet shape biscuit.

The bag 9 is placed into an insulated box 8 containing ice 11 to maintain the temperature of the solution 5 at between about 2° C. and 20° C. It will be appreciated that the appropriate temperature range can be maintained by refrigeration or other known mechanisms and, in addition, presently available microprocessor controls can be employed.

The bag 9 ideally is made of a material that is both mechanically and chemically stable and, for the system shown, is permeable both to $O_2$ and $CO_2$. A polyethylene and silicone composite can be employed to provide that mechanical stability and permeability, the polyethylene giving mechanical stability and the silicone giving permeability.

The molecular oxygen is needed to maximize the probability of the tissue to survive and, in addition, it permits some ingredients (e.g., coenzymes and antibiotics) in the biscuit 6 to function properly. The carbon dioxide is a by-product of tissue metabolism. Of course, the molecular oxygen can be provided by other mechanisms (e.g., $O_2$ cartridges, gas-evolving chemical reactions or electrical anodic liberation of oxygen). The carbon dioxide can be absorbed by other mechanisms (e.g., gascolators, chemisorbents).

To construct the bag 9, a back sheet 1 is attached to a front sheet 2 by a seal 3 disposed at the periphery of the sheets 1 and 2. A latch mechanism 4 is used to seal the bag 9 once the entire contents are present (i.e., the solution, the biscuit and the severed appendage). The seal is broken only when surgical re-implantation is imminent.

In addition to an electrolyte and a pH buffer, usually the biscuit will contain one or more of the following: an energy source (e.g., glucose and fructose); a high-energy phosphate compound (e.g., ATP and creatine phosphate); a metabolite (e.g., coenzymes and aminoacids); a material to remove toxic debris (activated charcoal and heavy metal chelators); a material to slow down tissue destruction (e.g., protease and peptidase inhibitors); a material to inactivate bacteria and viruses (e.g., antibiotics and methylene blue); a material to enhance survival in a cold environment (e.g., glycerol); a material to enhance survival during oxidative stress (e.g., glutathione and selenium, superoxide dismutase, carotene); and a material to enhance wound healing (e.g., zinc oxide).

Modification of the invention herein disclosed will occur to persons skilled in the art and all such modifications are deemed to be within the scope of the invention as defined by the appended claims.

What is claimed is:

1. A system to preserve both living tissue that has been severed from its host or living cells to be stored, cloned or hybridized, that comprises:

a gas-permeable bag capable of receiving the tissue, a quantity of liquid and a biscuit and further means to maintain a sterile environment therefor during storage of the tissue;

said biscuit disposed within the bag and in the liquid including both an electrolyte to help maintain cellular internal environment of the tissue and a pH buffer, said biscuit being precisely soluble in the liquid so as to provide a quasistatic biochemical environment; and means to maintain the liquid and tissue at a required temperature, said temperature being above the freezing point of the living tissue.

2. A system according to claim 1 in which the electrolyte includes at least one electrolyte taken from the group consisting of potassium bicarbonate, potassium chloride, potassium dihydrogen phosphate and calcium salts.

3. A system according to claim 1 or claim 2 in which the pH buffer includes at least one of the group consisting of sodium bicarbonate, potassium bicarbonate and their conjugate.

4. A system according to claim 1 in which the biscuit further includes a chemical energy source.

5. A system according to claim 4 in which the energy source is taken from the group consisting of glucose, fructose, and their polymers.

6. A system according to claim 1 in which the biscuit contains high-energy phosphate compounds.

7. A system according to claim 6 in which the high-energy phosphate compounds are taken from the group consisting of ATP and creatine phosphate.

8. A system according to claim 1 in which the biscuit contains a metabolite.

9. A system according to claim 8 in which the metabolite is taken from the group consisting of coenzymes and amino acids.

10. A system according to claim 1 in which the biscuit contains a material to remove toxic debris.

11. A system according to claim 10 in which the material to remove toxic debris are taken from the group consisting of activated charcoal and heavy metal chelators.

12. A system according to claim 1 in which the biscuit contains materials to decrease the rate of tissue destructions.

13. A system according to claim 12 in which the materials to decrease the rate of tissue destruction include at least one of protease, peptidase nuclease and lipase inhibitors.

14. A system according to claim 1 in which the biscuit contains a material that serves to inactivate bacteria and/or viruses.

15. A system according to claim 14 in which the material that serve to inactivate bacteria and/or viruses is taken from the group consisting of antibiotics and photodynamic dyes.

16. A system according to claim 1 in which the biscuit contains a material to enhance survival in a cold environment.

17. A system according to claim 16 in which said material is taken from the group consisting of glycerol and ethylene glycol.

18. A system according to claim 1 in which the biscuit contains a material to enhance survival of the tissue under oxidative stress.

19. A system according to claim 18 in which said material includes at least one of the group consisting of glutathione, selenium, superoxide dismutase, carotene and catalase.

20. A system according to claim 1 that includes a woundhealing agent.

21. A system according to claim 20 in which the woundhealing agent is zinc oxide.

22. A system as claimed in claim 1 in which the biscuit also contains glycerol to enhance resistance of the tissue to cold, zinc oxide to promote wound healing, reduced glutathione to enable the tissue to survive oxidation stress, and materials capable of absorbing and neutralizing toxins.

23. A system as claimed in claim 1 in which the means to maintain the liquid at a required temperature comprises an insulating enclosure to receive the bag and means to supply heat and to extract heat therefrom.

24. A system as claimed in claim 1 in which the bag is permeable to at least one of oxygen and carbon dioxide.

25. A system as claimed in claim 1 having means to produce oxygen-free radicals in part to aid in sterilization of the inside of the bag and the liquid therein.

26. A system according to claim 1 in which the means maintain the liquid and tissue at the required temperature includes a housing to receive the bag and related system elements.

27. For use in a system to preserve living tissue that has been severed from its host, which system includes a gas-permeable container to receive the living tissue and a liquid solution, a biscuit to be received by the liquid that also receives the tissue, which biscuit contains an electrolyte to maintain the cellular internal environment and a pH buffer, said biscuit being adapted to dissolve in a precise manner within the liquid to form a liquid solution that is quasistatic biochemically poised to maximize the probability of survival of the tissue.

28. A biscuit as defined by claim 27 that further contains glycerol to enhance resistance of the tissue to low temperatures, zinc oxide to promote wound healing, reduced glutathione to enable tissue to survice oxidative stress, and materials capable of absorbing neutralized toxins.

29. A biscuit according to claim 27 in which the electrolyte includes at least one electrolyte taken from the group consisting of potassium bicarbonate, potassium chloride, potassium dihydrogen phosphate and calcium salts.

30. A biscuit according to claim 27 or claim 29 in which the pH buffer includes at least one of the group consisting of sodium bicarbonate and potassium bicarbonate.

31. A biscuit according to claim 27 which includes an energy source.

32. A biscuit according to claim 31 in which the energy source is taken from the group consisting of glucose and fructose.

33. A biscuit according to claim 27 which contains high-energy phosphate compounds.

34. A biscuit according to claim 33 in which the high-energy phosphate compounds are taken from the group consisting of ATP and creatine phosphate.

35. A biscuit according to claim 27 which contains a metabolite.

36. A biscuit according to claim 35 in which the metabolites are taken from the group consisting of coenzymes and aminoacids.

37. A biscuit according to claim 27 which contains a material to remove toxic debris.

38. A biscuit according to claim 37 in which the materials to remove toxic debris are taken from group consisting of activated charcoal and heavy metal chelators.

39. A biscuit according to claim 27 which contains materials to decrease the rate of tissue destructions.

40. A biscuit according to claim 39 in which the materials to decrease the rate of tissue destruction include at least one of protease and peptidase inhibitors.

41. A biscuit according to claim 27 which contains materials that serves to inactivate bacteria and viruses.

42. A biscuit according to claim 41 in which the materials that serve to inactivate bacteria and viruses are taken from the group consisting of antibiotics and methylene blue.

43. A biscuit according to claim 27 which contains a material to enhance survival in a cold environment.

44. A biscuit according to claim 43 in which said material is glycerol.

45. A biscuit according to claim 27 which contains a material to enhance survival of the tissue under oxidative stress.

46. A biscuit according to claim 45 in which said material includes at least one of the group consisting of glutathione, selenium, superoxide dismutase and carotene.

47. A biscuit according to claim 27 that includes a woundhealing agent.

48. A biscuit according to claim 47 in which the woundhealing agent as zinc oxide.

49. A method of preserving living tissue that has been severed from its host, that comprises:

depositing the tissue in a gas-permeable container containing a sterile liquid;

introducing to the liquid within the container a biscuit containing a buffer and an electrolyte, which biscuit slowly dissolves in the liquid to form a liquid solution to provide a quasistatic biochemical environment most favorable to the metabolizing tissue, and maintaining the liquid at a temperature favorable to survival of the tissue, said temperature being above the freezing point of the living tissue of the tissue.

50. A method as claimed in claim 49 in which the temperature is in the range from about 2° C. to 20° C.

51. A method as claimed in claim 49 in which the liquid contains nutrients taken from the group consisting of glucose and aminoacids.

52. A method as claimed in claim 49 in which the liquid contains antioxidants taken from the group consisting of superoxide, and carotene.

53. A method as claimed in claim 49 in which the buffer is bicarbonate.

54. A method as claimed in claim 49 in which the electrolyte is calcium or potassium.

55. A method as claimed in claim 49 in which the liquid contains glycerol to provide thermal stability.

56. A method as claimed in claim 49 in which the liquid contains an antibiotic.

57. A method as claimed in claim 56 in which the antibiotic is taken from the group consisting of amphotericin, tetracycline, and methylene blue.

58. A method as claimed in claim 49 in which the liquid contains glutathione to serve as a reductant.

59. A method as claimed in claim 49 in which the liquid contains zinc oxide to provide trace metals.

60. A system as claimed in claim 1 having means to produce molecular oxygen in situ within the bag during storage of the tissue.

61. A system according to claim 1 in which the liquid and tissue are maintained at a temperature in the range from about 2 to 20 degrees C.

62. A biscuit according to claim 27 in which the biscuit is T-shaped to provide more uniform dissolution thereof.

63. A system according to claim 1 in which the biscuit is T-shaped to provide uniform dissolution thereof in the liquid.

64. A system according to claim 1 in which the bag is made of a material that is both mechanically and chemically stable and is permeable to both molecular $O_2$ and $CO_2$.

65. A system according to claim 64 in which the material is a polyethylene and silicone composite to provide the mechanical stability and permeability.

* * * * *